United States Patent [19]

Walsh

[11] Patent Number: 4,540,936

[45] Date of Patent: Sep. 10, 1985

[54] SOIL MOISTURE SENSOR

[75] Inventor: John E. Walsh, Box 264, Bradford, Vt. 05033

[73] Assignees: Dartmouth College; John E. Walsh, both of Hanover, N.H.

[21] Appl. No.: 416,232

[22] Filed: Sep. 7, 1982

[51] Int. Cl.³ .............................................. G01R 27/26
[52] U.S. Cl. .................................................... 324/61 P
[58] Field of Search .................. 324/61 P, 65 P, 61 R

[56] References Cited

U.S. PATENT DOCUMENTS

| | | | |
|---|---|---|---|
| 1,610,563 | 12/1926 | McIlvaine | 324/65 P |
| 2,083,074 | 6/1937 | Maass | 324/65 P |
| 2,304,448 | 12/1942 | Fletcher | 324/61 P |
| 2,870,404 | 1/1959 | Oxley | 324/65 P |
| 3,123,751 | 3/1964 | Balsbaugh | 324/61 P |
| 3,209,247 | 9/1965 | Mead et al. | 324/61 R |
| 3,243,365 | 3/1966 | Aikin | 324/65 P |
| 3,437,924 | 4/1969 | Tocanne | 324/61 P |
| 3,803,570 | 4/1974 | Barlow et al. | 324/61 R X |
| 4,050,016 | 9/1977 | Marsh et al. | 324/61 R |
| 4,209,740 | 6/1980 | Marthe et al. | 324/61 P X |
| 4,288,742 | 9/1981 | Walsh | 324/61 R |
| 4,389,900 | 6/1983 | Gutierrez | 324/61 P X |

FOREIGN PATENT DOCUMENTS

| | | | |
|---|---|---|---|
| 0270674 | 10/1966 | Australia | 324/61 P |
| 0178475 | 5/1954 | Austria | 324/65 P |
| 0517212 | 2/1931 | Fed. Rep. of Germany | 324/65 P |

*Primary Examiner*—Stanley T. Krawczewicz
*Attorney, Agent, or Firm*—Cushman, Darby & Cushman

[57] ABSTRACT

A moisture sensor including in one embodiment a probe formed with a first cylindrical tube extending outward from a base and having a plurality of axially extending slots around the periphery thereof and a second slotted cylindrical tube extending outward from the base separated and insulated from the first tube, and extending coaxially with the first tube. The tubes form an effective coaxial capacitor and are insertable into material to be sensed appear as a ground plane. In a second and third embodiment a member defining flat surfaces extends from a base forming in cross-section a volume with a square center and legs extending from each side thereof to an open peripheral end. An RC bridge circuit, preferably a Wien bridge or a capacitor divider circuit is connected to the tubes to measure the impedance of the material.

14 Claims, 11 Drawing Figures

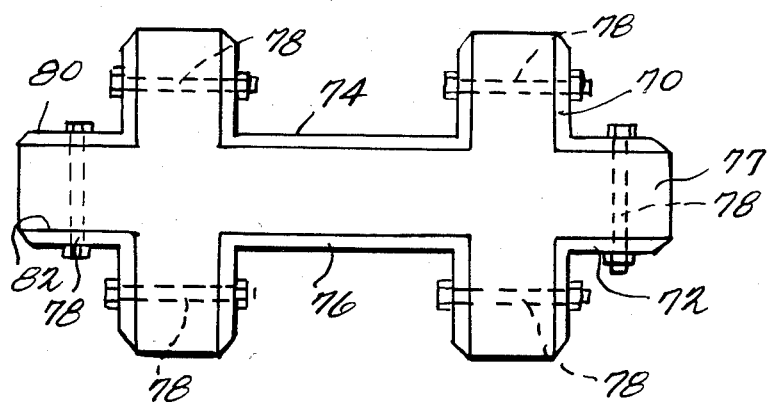
FIG. 7
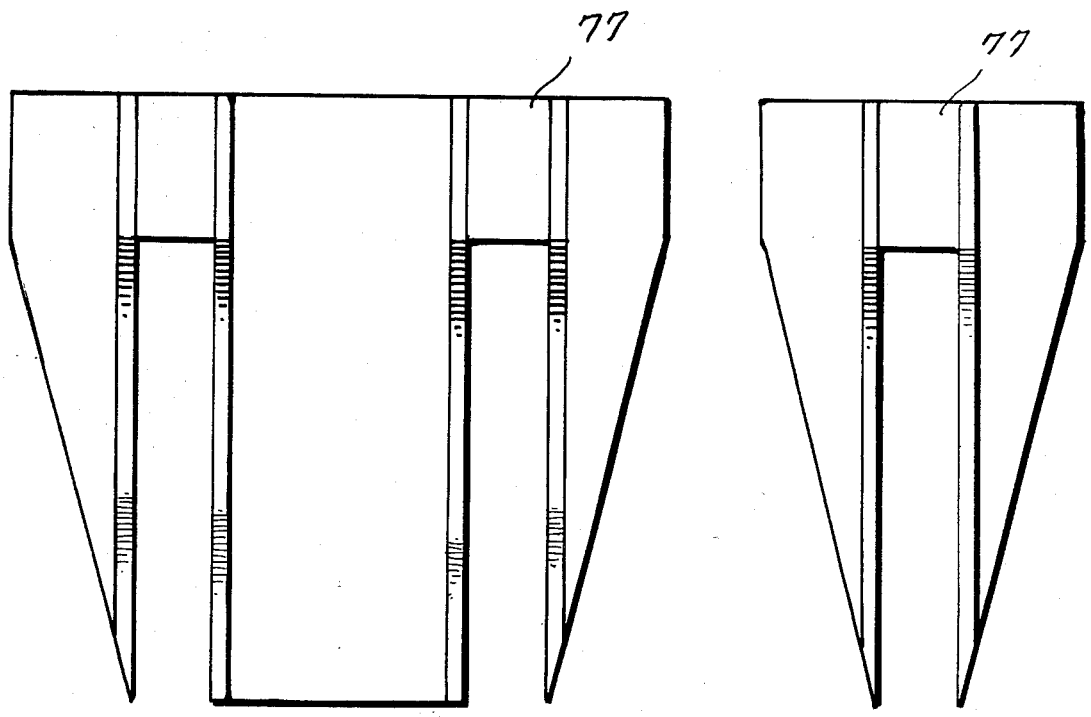
FIG. 8
FIG. 9

SOIL MOISTURE SENSOR

BACKGROUND AND SUMMARY OF THE INVENTION

The present invention relates to an improved sensor for producing a signal indicating the moisture content of material into which the sensor is inserted.

Many applications exist in which it is necessary to accurately ascertain the moisture content of material. For example, knowing the exact moisture content of soil is important in agricultural applications, in waste treatment applications where soil is used for purifying water, for erosion studies, for monitoring earth dams, and for various military applications. Accurately determining the moisture content of grain is another important application. Maintaining accurate records as to the amount of moisture in trees is not only important in preventing forest fires, but also in monitoring the growth of those trees. Many other industrial applications such as curing concrete also require periodic and accurate information as to the moisture content of material.

Typically, moisture sensing devices in the past have included a container into which the material is placed, with plates or the like therein for determining the capacitance of the material placed therein and relating that capacitance to the moisture content. For example, the U.S. Pat. No. 3,209,247 to Mead and the U.S. Pat. No. 4,050,016, to Marsh et al show typical devices of this sort. These devices are, however, inconvenient to use since they require removing a portion of the material to be tested. Further, removing the material, for example, digging a sample of soil, necessarily changes its density so that the measured results are not necessarily the actual moisture content of the soil before its removal.

Another inaccuracy arises in many of these devices because they measure only the capacitance of the soil or measure only the resistance. U.S. Pat. No. 3,803,570 to Barlow et al describes a capacitance measuring device. None of these capacitance devices however have effectively combined high accuracy with ease of use. The U.S. Pat. No. 2,870,404 to Oxley describes a resistive measuring device in which a plurality of spikes are inserted into the ground. In fact, both the resistance and capacitance of the soil vary with moisture and vary independently of each other depending upon soil condition. The relation of resistance to moisture particularly is non-linear and very difficult to predict for any given composition. Devices which ignore variation of resistance with capacitance necessarily produce an inaccurate indication of moisture content.

My U.S. Pat. No. 4,288,742 issued Sept. 8, 1981 discloses a unique, simple, and effective moisture sensor which can be inserted easily into material to be measured, usually without damage to that material, and which takes into account both resistance and capacitance to produce an accurate indication of moisture content. The sensor includes a probe having at least a single, and preferably a plurality of spines extending outward from a base so that the spines can be inserted into the material. The spines are sufficient in number to appear as a ground plane forming an effective coaxial capacitor. Inaccuracies resulting from fringing fields are eliminated while the device remains easily insertable.

The impedance produced by the material surrounding the spines forms part of an RC bridge, preferably a Wien or other bridge, which also includes a separate resistor and capacitor. Thus, the impedance of the material, both its capacitance and resistance, are measured to produce signals indicating that impedance. By determining the ratio of the voltages across the RC circuit forming part of the bridge and the RC circuit of the material impedance and determining the resonant frequency, both the resistance and capacitance of the soil can be determined and related to the dielectric constant of the material. From that dielectric constant the soil moisture content can be easily determined according to well known relations.

The co-axial geometry accurately defines the active volume by minimizing fringe volumes. With sensors of the type which use plates, the fringe capacitances introduce errors since those capacitances vary with the dielectric constant. The co-axial geometry has no such fringe capacitance, except at the ends. A first ring of spines extend outwardly from a base in parallel with a second ring of spines extending outwardly from the base, also in parallel, and within the first ring, separated and insulated electrically therefrom. The two rings thus form an effective coaxial capacitor which can be inserted into the material to be sensed.

While the sensor described in the above-mentioned patent is quite satisfactory and superior to other techniques generally reviewed above, the use of individual spines to form the coaxial capacitor has at least two disadvantages. First, the configuration is somewhat difficult to mechanically construct. The individual spines must be formed and accurately attached in a permanent way to a metal or other ring or the like. Second, there is some possibility of dislocation of the spines as they are pushed into the ground and perhaps encounter some object or, for some other reason, are slightly displaced. This displacement also produces some inaccuracies in the final output although such inaccuracies are not necessarily unacceptable.

The present invention relates to an improved moisture sensor in which these above-noted difficulties are eliminated by the use of a member extending outwardly from a base to define extending surfaces which partially bound a volume containing the media when inserted. An opening is provided between the volume and the media outside the sensor to permit movement of moisture therethrough and also make insertion easier.

In one embodiment two slotted cylindrical tubes are mounted coaxially and replace the spines described in the above-mentioned application. The cylinders are sharpened on the end which pushes into the ground. A simple insulating plug can be used to mount and electrically separate the two sensors. Since the cylinders have greater rigidity than the previously used spines, the small problem of displacement does not occur as readily. Forming slots in the cylinders is a much easier machining process than forming and mounting the spines as in the previous approach.

In a second embodiment the volume is partially bounded by a cross-shaped member having flat surfaces defining the volume in cross-section as a square center with a rectangular leg extending from each side thereof. Each leg is open at the peripheral edge. The member and the volume in the legs tapers in the longitudinal direction so that at the insertion end the volume is made up only of the center section. A plurality of parallel plate capacitors are thereby formed by the parallel facing surfaces which are driven at the same potential. The four legs provide not only a controlled volume but good mechanical rigidity. The outer part of each leg can be insulated from the rest of the member if desired to serve as a guard ring.

In a third embodiment two cross-shaped members are joined together at the peripheral edge of one leg of each. This gives better definition of the electrical volume since more of the volume is remote from openings and therefore less susceptable to fringe effects.

Many other objects and purposes of the invention will be clear from the following detailed description of the drawings.

BRIEF DESCRIPTION OF THE DRAWINGS

FIG. 7 shows a top plan view of a third embodiment;

FIG. 8 shows a side view of the third embodiment;

FIG. 9 shows an end view of the third embodiment;

DETAILED DESCRIPTION OF THE DRAWINGS

Figure 1:
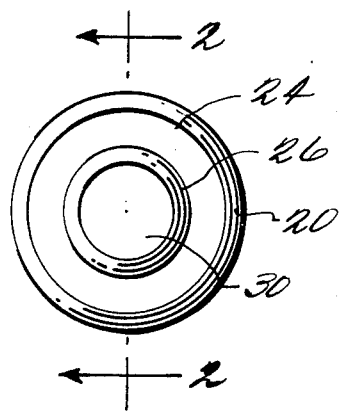
FIG. 1 shows an end view of the improved sensor of the present invention.
Figure 2:
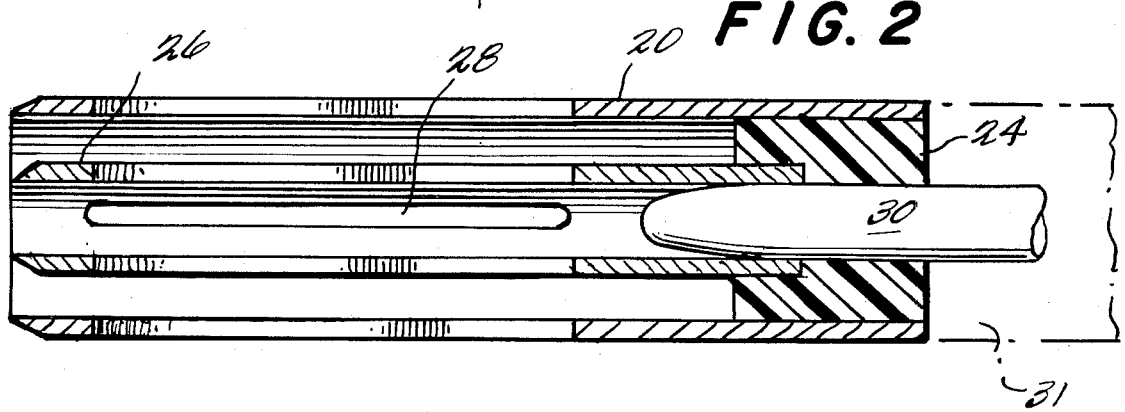
FIG. 2 shows a sectional view of the sensor of FIG. 1 along the lines 2—2.
Figure 3:
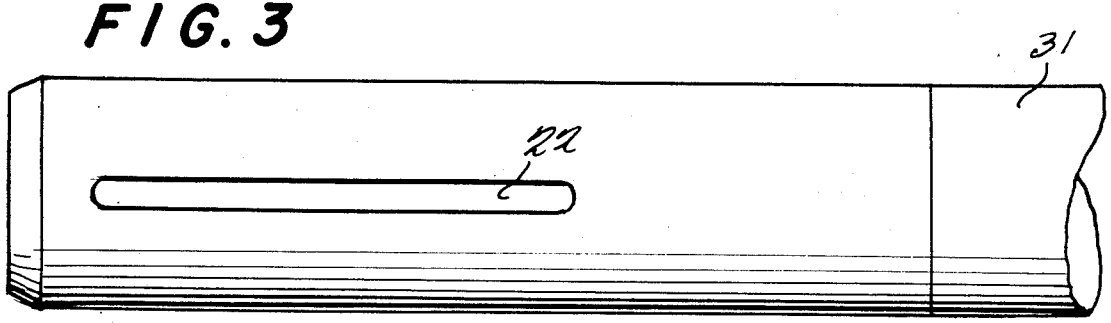
FIG. 3 shows a side view of the sensor of FIGS. 1 and 2.

Reference is now made to FIGS. 1-3 which illustrate one embodiment of the improved soil sensor of the present invention. In this embodiment, a first cylindrical tube 20 having a plurality, for example four, slots 22 therein is mounted on an insulating plug 24. The slots extend in an axial direction and are separated from each other around the periphery of the tube. Tube 20 is pressed fitted onto insulating plug 24, for example of a plastic or other similar material. Plug 24 thereby defines a base for the sensor. A second tube 26 likewise is provided with a plurality of slots 28 extending coaxially and distributed around the periphery of tube 26. Tube 26 may also be provided with four slots. The length and width of the slots is not critical and are chosen in accordance with desired mechanical characteristics of the device. Preferably, the cylinders are slotted over most of their length. A slot width between ⅛ and 3/16 inch is satisfactory. The slots in effect divide the tubes into a plurality of separated capacitive regions which when properly excited as disclosed below, provide a signal indicating the impedance of the medium into which the sensor has been inserted in the same fashion as the above-described previous device utilizing spines. Tubes 20 and 26 are preferably sharpened on the end to facilitate insertion. Cylindrical tube 26 is also press fitted onto plug 24 in the same fashion as tube 20.

The electrical output of the tubes is coupled by a center conductor 30 to an on board electronic circuit generally indicated in FIGS. 1-3 as 31. The circuit can include a calibrated display indicating volumetric moisture content. Alternatively the data can be transmitted and processed remotely.

The cylinders can be sized according to the desired application. A length of 2 to 10 inches for both cylinders and diameters of 1 to 4 inches and ½ to ¾ inch for the outer and inner cylinders, respectively, should be satisfactory. Any metal which is not chemically reactive can be used for the cylinders. Thin walled aluminum or stainless steel are satisfactory. The tubes need only be thick enough to provide sufficient mechanical rigidity for insertion.

Figure 4:
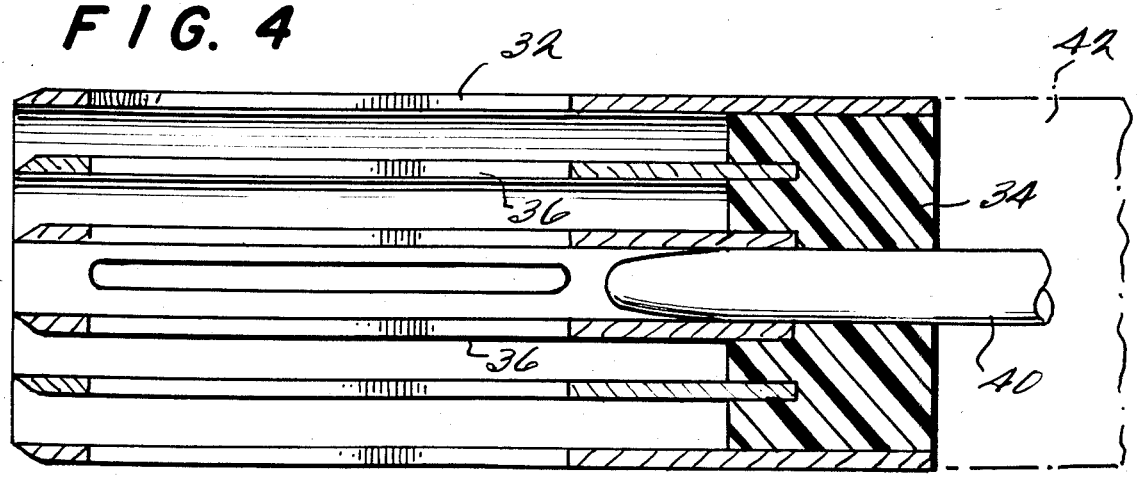
FIG. 4 shows a modification of the first embodiment with a third cylindrical tube mounted about the tubes which form the coaxial capacitor and providing protection against a stray capacitance.

In order to guard against stray capacitance, a third metal cylinder 32, which need not be slotted, can be press fitted or otherwise attached to a plug 34 as shown in FIG. 4. Plug 34 in the same fashion with respect to the embodiment of FIGS. 1-3 mounts the slotted tubes 36 and 38 with a center conductor 40 coupling the output signal to the electronic circuitry 42.

Figure 5:
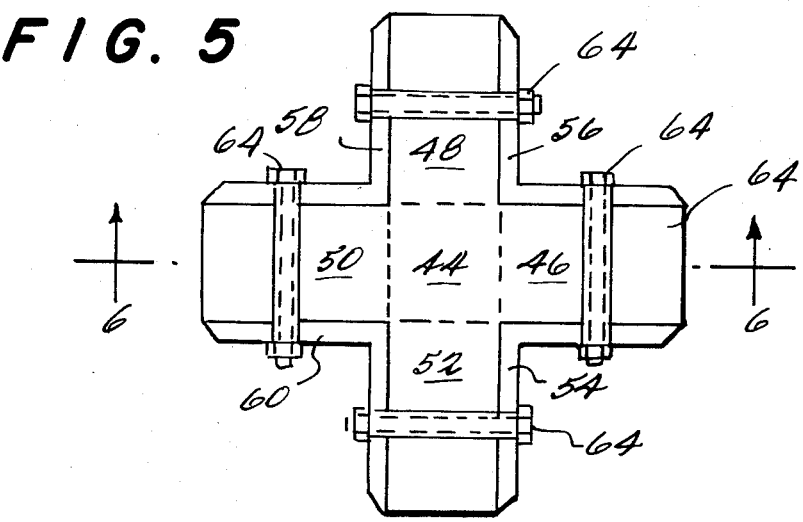
FIG. 5 shows a top plan view of a second embodiment of the present invention.
Figure 6:
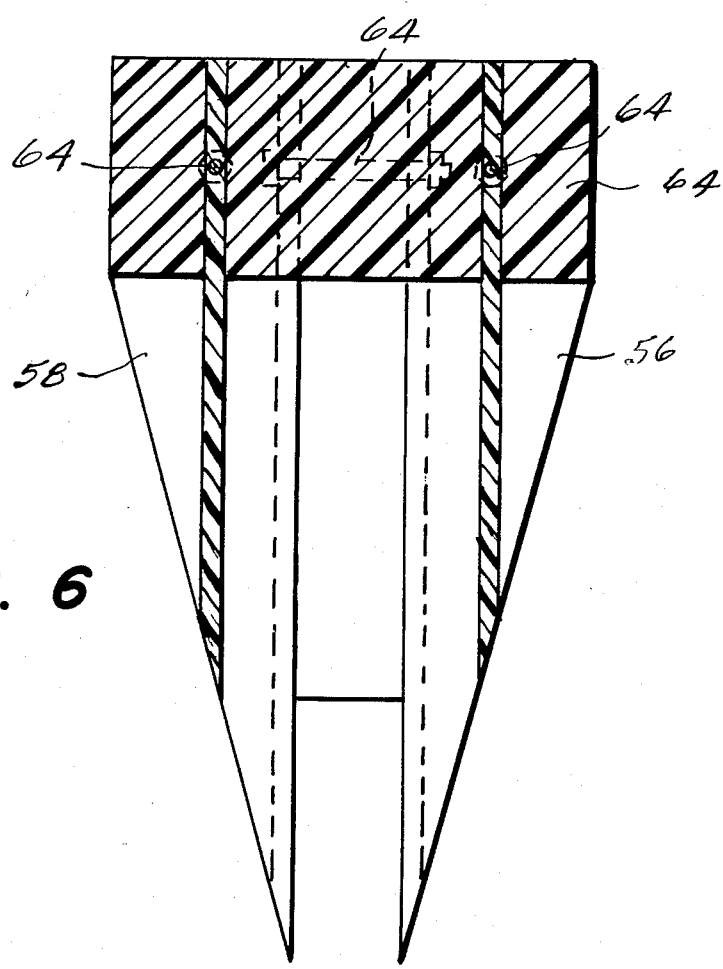
FIG. 6 shows a sectional view along the lines 6—6 in FIG. 5.

Referring to FIGS. 5 and 6 the second embodiment of the invention is formed by a member defining flat surfaces extending parallel to provide the capacitances. More particularly the member defines the volume in cross-section as a center square 44 with legs 46, 48, 50 and 52 extending outwardly therefrom. Each leg is open at the peripheral end. L-shaped metal plates 54, 56, 58 and 60 are tapered as can be seen in FIG. 5 and bound the measuring volume. A plastic plug 64 fills the volume at the upper end of the member and the L-shaped pieces are attached thereto. Electrical connection to the capacitances thus formed can be carried out in any way, for example as in the first embodiment. The outer portions or each L-shaped plate are electrically insulated from the inner portions where screws 64 extend therethrough to provide a guard ring functioning in the same way as the ring in FIG. 4.

FIGS. 7, 8 and 9 show a third embodiment in which two of the cross-shaped volumes of the embodiment of FIGS. 5 and 6 are combined along the peripheral edges of respective legs. L-shaped plates 70 and 72 are fastened to U-shaped plates 74 and 76 to each other and to plug 77 by insulating screws and bolts 78 as in the second embodiment. U-shaped plates 74 and 76 are similarly fastened to L-shaped plates 80 and 82 to each other and to plug 77 by screws and bolts 78. This arrangement provides much greater internal volume remote from the six open ends of the legs and therefore is less susceptible to fringe effects. A guard ring can be provided as in FIGS. 7 and 8 or the four L-shaped plates can serve that function. The structure and function is otherwise the same as in the second embodiment.

Figure 10:
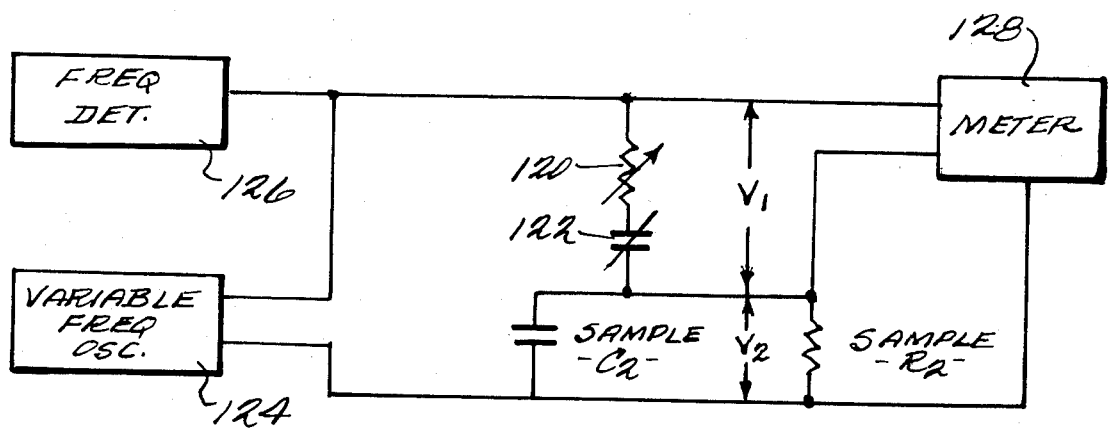
FIG. 10 shows an electrical schematic of one circuit for measuring the impedance of the soil.

FIG. 10 shows one circuit for producing signals which can be utilized to determine moisture content. Variable resistance 120 and capacitance 122 combine with the capacitance and resistance of the material into which the probe is inserted to form a Wien bridge. The bridge is coupled to a conventional variable frequency oscillator 124 and the bridge is utilized conventionally to determine both the resonant frequency by way of a frequency detector 126 and the voltage ratio by way of meter 128. The resonant frequency W is determined by the following relation:

$$W^2 = \frac{1}{R_1 R_2 C_1 C_2}$$

wherein:

$R_1$ and $C_1$ are the resistance and capacitance, respectively, of the bridge elements; and $R_2$ and $C_2$ are the resistance and capacitance, respectively, of the material. The voltage ratio is determined by the following relation:

$$\frac{V_2}{V_1} = \frac{1}{1 + \frac{C_2}{C_1} + \frac{R_1}{R_2}}$$

Solving these two equations, either manually with the aid of a calculator, or automatically by a micro-processor or otherwise, gives the capacitance and resistance of the sample, and these figures can then be easily used to calculate the dielectric constant. The dielectric constant can then be related to the moisture content using known relations. The operating frequency can be chosen as convenient. Typically, however, a frequency in the range of 1 to 100 Mhz would be selected.

Figure 11:
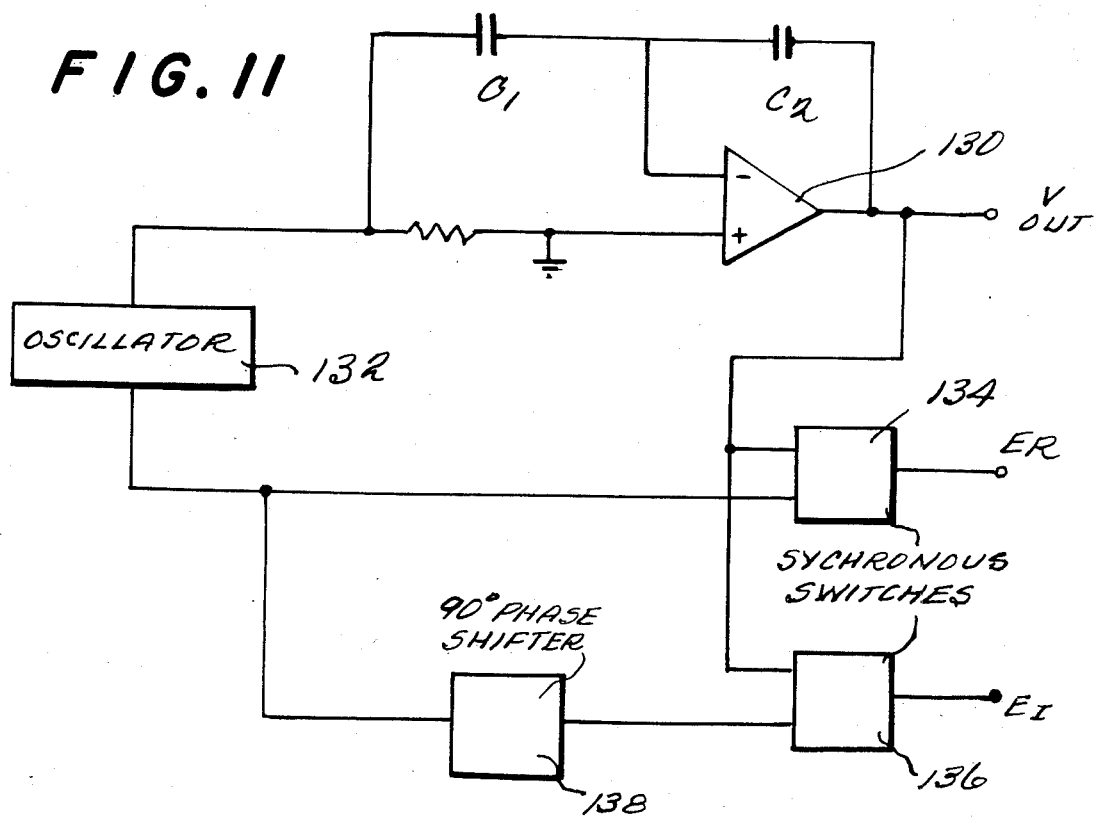
FIG. 11 shows a second circuit for measuring impedance.

FIG. 11 illustrates a second circuit which can be used to produce an electrical signal indicating the moisture content of the soil or other medium. The circuitry of FIG. 11 is a capacitive divider read-out circuit in which two capacitors $C_1$ and $C_2$ are connected to a high gain operational amplifier 130. A suitable oscillator 132 provides an alternating current signal at a suitable frequency which is applied to the positive input to operational amplifier 130 while the negative input is connected to the junction between capacitor $C_1$ and $C_2$. The serially connected capacitors bridge the positive input to operational amplifier 130 and the output thereof. The output of operational amplifier 130 thereby indicates the ratio of the capacitances. Switches 134 and 136 provide outputs respectively indicating the resistive and capacitive portions of the output. Oscillator 132 is connected to switches 134 and 136 directly and through phase shifter 138. The circuit will produce an accurate output even if the material has a complex dielectric function.

In materials where the resistance is very large, for example, trees, it may be possible to ignore the resistance value and accordingly only the resonant frequency would need to be measured. In such an application, it may also be desirable to add another resistance and capacitance in parallel with the capacitance and resistance provided by the material to provide wider control of the operating frequency. As an alternative to utilizing a separate oscillator, a conventional Wien bridge oscillator can be utilized in such circumstances where resistance can be ignored. By variation of the frequency, a considerable range of frequencies can be examined to accurately determine the dispersive properties of the material.

If desired, to determine the rate of penetration of moisture through a material several probes can be inserted in parallel at different levels of the material.

Many changes and modifications can, of course, be made in the above-described embodiment of the invention. If desired other conditions such as temperature can be sensed and processed. Accordingly, that embodiment is intended to be limited only by the scope of the appended claims.

What is claimed is:

1. A moisture sensor for insertion into a moisture containing media comprising:

a base;

means extending outwardly from said base including first and second slotted tubes forming an effective coaxial capacitor defining adjacent extending surfaces partially bounding at least one volume containing said media when said sensor is inserted, said bounding surfaces providing an extending opening between said volume and the media therein and the media outside said sensor; and circuit means connected to said means extending outwardly for applying an ac signal thereto to measure the impedance between said surfaces in the region where the opening extends and thereby the moisture content of said media.

2. A sensor as in claim 1 wherein said means extending outwardly terminates at the end remote from said base in a sharp edge which can be inserted into said media.

3. A moisture sensor for insertion into a moisture containing media comprising:

a base; means extending outwardly from said base for insertion into said media and defining an internal volume with extending openings to the media outside said volume and a capacitance; and circuit means connected to said means extending outwardly for applying an ac signal to said means extending outwardly for measuring the impedance of the media in said volume in the region where the opening extends and thereby the moisture content, including a capacitance dividing circuit.

4. A moisture sensor comprising:

a base;

a first cylindrical tube extending outwardly from said base and having a plurality of axially extending slots around the periphery thereof;

a second cylindrical tube extending outwardly from said base coaxially within said first tube and having a plurality of axially extending slots around the periphery thereof, separated and electrically insulated therefrom, said tubes defining ground planes and forming an effective coaxial capacitor and being insertable into material to be sensed; and circuit means connected to said first and second tubes for applying an ac signal to said tubes for measuring the impedance of said material between said rings.

5. A sensor as in claim 4 wherein said base is a plastic plug onto which said tubes are press fitted.

6. A sensor as in claim 4 wherein one end of each of said tubes remote from said base is sharpened to facilitate insertion.

7. A sensor as in claim 4 further including an outer cylindrical tube extending coaxially with said first and second tubes for guarding against stray capacitance.

8. A sensor as in claim 1 or 4 wherein said circuit means includes a capacitance dividing circuit.

9. A sensor as in claim 1 or 4 wherein said circuit means includes a Wein bridge.

10. A moisture sensor for insertion into a moisture containing media comprising:

a base;

a plurality of plates attached to said base and extending outwardly therefrom to define at least one cross-shaped volume with four legs extending outward form a central portion to an open peripheral edge, the end of said plates remote from said base being insertable into said media, said plates defining a plurality of pairs of parallel extending surfaces with each pair defining a capacitor; and circuit means connected to said plates for applying an ac signal thereto to measure the impedance of said capacitors and thereby the moisture content of said media.

11. A sensor as in claim 10 wherein said plates are L-shaped to form a single cross-shaped volume.

12. A sensor as in claim 10 wherein said plates are L-shaped and U-shaped to form a volume of two crosses connected at the ends of respective legs.

13. A sensor as in claim 10 wherein said circuit means includes a Wein bridge.

14. A sensor as in claim 10 wherein said circuit means includes a capacitance dividing circuit.

* * * * *